US011819255B2

(12) United States Patent
Ensign et al.

(10) Patent No.: US 11,819,255 B2
(45) Date of Patent: Nov. 21, 2023

(54) TETHER TENSIONING INSTRUMENTATION AND RELATED METHODS

(71) Applicant: Ortho Development Corporation, Draper, UT (US)

(72) Inventors: Michael D. Ensign, Salt Lake City, UT (US); Bao-Khang Ngoc Nguyen, Salt Lake City, UT (US)

(73) Assignee: Ortho Development Corporation, Draper, UT (US)

( * ) Notice: Subject to any disclaimer, the term of this patent is extended or adjusted under 35 U.S.C. 154(b) by 899 days.

(21) Appl. No.: 16/594,709

(22) Filed: Oct. 7, 2019

(65) Prior Publication Data

US 2021/0100598 A1 Apr. 8, 2021

(51) Int. Cl.
*A61B 17/88* (2006.01)
*A61B 17/70* (2006.01)
(Continued)

(52) U.S. Cl.
CPC ...... *A61B 17/8869* (2013.01); *A61B 17/7053* (2013.01); *A61B 17/7083* (2013.01);
(Continued)

(58) Field of Classification Search
CPC ............ A61B 17/8869; A61B 17/8861; A61B 17/7053; A61B 17/7083
See application file for complete search history.

(56) References Cited

U.S. PATENT DOCUMENTS 1,346,940 A * 7/1920 Collins .............. A61B 17/8869
606/103
4,156,574 A 5/1979 Boden
(Continued)

FOREIGN PATENT DOCUMENTS

AU 2014203469 A1 7/2014
AU 2014201336 A1 10/2014
(Continued)

OTHER PUBLICATIONS

Feb. 4, 2021, PCT/US2020/054610, International Search Report (3 pgs).
(Continued)

*Primary Examiner* — Jan Christopher L Merene
*Assistant Examiner* — Anna V. Little
(74) *Attorney, Agent, or Firm* — Matthew D. Thayne; Thayne and Davis LLC

(57) ABSTRACT

Tether tensioning instruments, such as instruments used to tension and/or lock a tether about a spinal feature to assist in spinal fixation, and related methods and systems. In some embodiments, the instrument may comprise a handle, a tensioner base coupled with the handle, at least a portion thereof being movably coupled to the handle, and a tether coupling member coupled with the tensioner base and configured to fixedly engage a tether. The instrument may further comprise a tensioner tip movably coupled with the tensioner base, wherein at least a portion of the tensioner base is biased away from the tensioner tip, and wherein the instrument is configured to allow for step-wise movement of the tensioner tip away from the tensioner base to increase tension between the tether and an element of the spinal fixation system.

13 Claims, 8 Drawing Sheets

(51) Int. Cl.
*A61B 17/00* (2006.01)
*A61B 17/56* (2006.01)

(52) U.S. Cl.
CPC ... *A61B 17/8861* (2013.01); *A61B 2017/0042* (2013.01); *A61B 2017/00367* (2013.01); *A61B 2017/564* (2013.01)

(56) References Cited

U.S. PATENT DOCUMENTS

| | | | |
|---|---|---|---|
| 4,732,180 A | | 3/1988 | Fixel |
| 5,304,178 A | | 4/1994 | Stahurski |
| 5,312,410 A | * | 5/1994 | Miller .................... B25B 25/00 606/103 |
| 5,383,905 A | | 1/1995 | Golds et al. |
| 5,413,576 A | | 5/1995 | Rivard |
| 5,582,612 A | | 12/1996 | Lin |
| 5,702,399 A | | 12/1997 | Kilpela et al. |
| 5,980,473 A | * | 11/1999 | Korakianitis .......... A61B 17/88 600/587 |
| 6,053,921 A | * | 4/2000 | Wagner .............. A61B 17/8869 606/103 |
| 6,086,590 A | | 7/2000 | Margulies et al. |
| 6,391,030 B1 | | 5/2002 | Wagner et al. |
| 6,514,255 B1 | | 2/2003 | Ferree |
| 6,595,994 B2 | | 7/2003 | Kilpela et al. |
| 6,656,185 B2 | | 12/2003 | Gleason et al. |
| 6,689,140 B2 | | 2/2004 | Cohen |
| 6,695,852 B2 | * | 2/2004 | Gleason .................. B25B 25/00 606/103 |
| 7,207,090 B2 | | 4/2007 | Mattchen |
| 7,326,222 B2 | | 2/2008 | Dreyfuss et al. |
| 7,481,828 B2 | | 1/2009 | Mazda et al. |
| 7,828,830 B2 | | 11/2010 | Thramann et al. |
| 7,959,654 B2 | | 6/2011 | Mazda et al. |
| 8,096,998 B2 | | 1/2012 | Cresina |
| 8,162,946 B2 | | 4/2012 | Baccelli et al. |
| 8,172,843 B2 | | 5/2012 | Baccelli et al. |
| 8,221,464 B2 | | 7/2012 | Belliard et al. |
| 8,257,367 B2 | | 9/2012 | Bryant et al. |
| 8,323,294 B2 | | 12/2012 | Mickiewicz et al. |
| 8,323,318 B2 | | 12/2012 | Baccelli et al. |
| 8,323,319 B2 | | 12/2012 | Mazda et al. |
| 8,353,962 B2 | | 1/2013 | Eckman |
| 8,430,918 B2 | | 4/2013 | Baccelli et al. |
| 8,465,495 B2 | | 6/2013 | Belliard |
| 8,469,966 B2 | | 6/2013 | Allen et al. |
| 8,469,967 B2 | | 6/2013 | Pratt et al. |
| 8,496,660 B2 | | 7/2013 | Carl et al. |
| 8,636,770 B2 | | 1/2014 | Hestad et al. |
| 8,721,689 B2 | | 5/2014 | Butler et al. |
| 8,728,083 B2 | | 5/2014 | Baccelli et al. |
| 8,747,405 B2 | | 6/2014 | Belliard |
| 8,801,759 B2 | | 8/2014 | Mazda et al. |
| 8,814,910 B2 | | 8/2014 | Baccelli et al. |
| 8,828,055 B2 | | 9/2014 | Blain et al. |
| 8,870,870 B2 | | 10/2014 | Baccelli et al. |
| 8,906,068 B1 | | 12/2014 | Bedor |
| 8,945,188 B2 | | 2/2015 | Rezach et al. |
| 8,961,572 B2 | | 2/2015 | Kim et al. |
| 8,979,908 B2 | | 3/2015 | Lee et al. |
| 8,984,720 B2 | | 3/2015 | Gephart |
| 9,039,708 B2 | | 5/2015 | Larroque-Lahitette |
| 9,039,711 B2 | | 5/2015 | Mickiewicz et al. |
| 9,078,644 B2 | | 7/2015 | Stone |
| 9,084,644 B2 | | 7/2015 | Knueppel |
| 9,084,645 B2 | | 7/2015 | Knueppel |
| 9,101,406 B2 | | 8/2015 | Belliard |
| 9,101,425 B2 | | 8/2015 | Douget et al. |
| 9,107,720 B2 | | 8/2015 | Pratt et al. |
| 9,113,963 B2 | | 8/2015 | Baccelli et al. |
| 9,113,966 B2 | | 8/2015 | Baccelli et al. |
| 9,119,675 B2 | | 9/2015 | Lee et al. |
| 9,144,440 B2 | | 9/2015 | Aminian |
| 9,186,185 B2 | | 11/2015 | Hestad et al. |
| 9,192,367 B2 | | 11/2015 | Nunley et al. |
| 9,204,902 B2 | | 12/2015 | Belliard et al. |
| 9,204,903 B2 | | 12/2015 | Belliard et al. |
| 9,216,047 B2 | | 12/2015 | Bryant et al. |
| 9,295,496 B2 | | 3/2016 | Le Couedic et al. |
| 9,314,275 B2 | | 4/2016 | Clement et al. |
| 9,333,021 B2 | | 5/2016 | Gephart |
| 9,345,465 B2 | | 5/2016 | Aldridge et al. |
| 9,370,390 B2 | | 6/2016 | Mickiewicz et al. |
| 9,393,051 B2 | | 7/2016 | Baccelli et al. |
| 9,402,666 B2 | * | 8/2016 | Al Shail ............ A61B 17/7059 |
| 9,433,441 B2 | | 9/2016 | George et al. |
| 9,492,207 B2 | | 11/2016 | Baccelli et al. |
| 9,579,127 B2 | | 2/2017 | Kostuik et al. |
| 9,585,705 B2 | | 3/2017 | Koch et al. |
| 9,668,774 B2 | | 6/2017 | Larroque-Lahitette |
| 9,675,386 B2 | | 6/2017 | Akbarnia et al. |
| 9,707,025 B2 | | 7/2017 | Cavallazzi |
| 9,717,536 B2 | | 8/2017 | Baccelli et al. |
| 9,757,167 B2 | | 9/2017 | Hsu et al. |
| 9,775,651 B2 | | 10/2017 | Le Couedic et al. |
| 9,833,275 B2 | | 12/2017 | Mickiewicz et al. |
| 9,848,921 B2 | | 12/2017 | Mazda et al. |
| 9,872,713 B2 | | 1/2018 | Simpson et al. |
| 9,901,377 B2 | | 2/2018 | Legallois |
| 9,907,598 B2 | | 3/2018 | Feibel et al. |
| 9,949,778 B2 | | 4/2018 | Baccelli et al. |
| 9,993,351 B2 | | 6/2018 | Carl et al. |
| 9,999,450 B2 | | 6/2018 | Hsu et al. |
| 10,022,159 B2 | | 7/2018 | Simpson |
| 10,034,692 B2 | | 7/2018 | Palmer et al. |
| 10,052,143 B2 | | 8/2018 | Hulliger |
| 10,070,906 B2 | | 9/2018 | Douget et al. |
| 10,188,429 B2 | | 1/2019 | Carlson et al. |
| 10,231,765 B2 | | 3/2019 | Al Shail et al. |
| 10,278,746 B2 | | 5/2019 | Deneuvillers et al. |
| 10,314,635 B2 | | 6/2019 | Gephart |
| 10,426,537 B2 | | 10/2019 | Baccelli et al. |
| 10,433,878 B2 | | 10/2019 | Deneuvillers |
| 10,485,600 B2 | | 11/2019 | Gephart et al. |
| 10,499,972 B2 | | 12/2019 | Bosshard et al. |
| 10,568,673 B2 | | 2/2020 | Palagi et al. |
| 10,595,904 B2 | | 3/2020 | Albert et al. |
| 10,595,920 B2 | | 3/2020 | Simpson et al. |
| 10,603,078 B2 | | 3/2020 | Simpson et al. |
| 2002/0035366 A1 | | 3/2002 | Walder et al. |
| 2002/0072753 A1 | * | 6/2002 | Cohen ................ A61B 17/8861 606/103 |
| 2004/0199169 A1 | * | 10/2004 | Koons ................ A61B 17/8869 606/103 |
| 2004/0243131 A1 | | 12/2004 | Dirks et al. |
| 2005/0177179 A1 | | 8/2005 | Baynham et al. |
| 2005/0234471 A1 | * | 10/2005 | Schmucki ............. A61B 17/66 606/99 |
| 2006/0271055 A1 | | 11/2006 | Thramann |
| 2009/0082821 A1 | | 3/2009 | Konno et al. |
| 2009/0138048 A1 | | 5/2009 | Baccelli et al. |
| 2009/0248077 A1 | * | 10/2009 | Johns .................... A61B 17/707 606/301 |
| 2010/0042106 A1 | * | 2/2010 | Bryant ............... A61B 17/8869 606/103 |
| 2010/0298829 A1 | * | 11/2010 | Schaller ................ A61B 17/82 606/74 |
| 2011/0238118 A1 | | 9/2011 | Baccelli et al. |
| 2011/0245875 A1 | | 10/2011 | Karim |
| 2011/0288589 A1 | | 11/2011 | Fielding et al. |
| 2012/0143207 A1 | | 6/2012 | Belliard et al. |
| 2012/0197257 A1 | * | 8/2012 | Knueppel .......... A61B 17/8863 606/74 |
| 2012/0232533 A1 | * | 9/2012 | Veldman ............ A61B 17/8869 606/1 |
| 2012/0271354 A1 | | 10/2012 | Baccelli et al. |
| 2012/0303121 A1 | | 11/2012 | Douget et al. |
| 2012/0323280 A1 | | 12/2012 | Chin et al. |
| 2013/0237990 A1 | | 9/2013 | Nunley et al. |
| 2013/0261625 A1 | | 10/2013 | Koch et al. |
| 2013/0261668 A1 | | 10/2013 | Douget et al. |
| 2013/0261680 A1 | | 10/2013 | Baccelli et al. |

(56) References Cited

U.S. PATENT DOCUMENTS

| | | | |
|---|---|---|---|
| 2014/0074172 A1 | 3/2014 | Lee et al. | |
| 2014/0100573 A1* | 4/2014 | Llas Vargas | A61B 17/8869 606/74 |
| 2014/0114356 A1 | 4/2014 | Le Couedic et al. | |
| 2014/0148854 A1 | 5/2014 | Carlson et al. | |
| 2014/0214040 A1 | 7/2014 | Carl et al. | |
| 2014/0257397 A1 | 9/2014 | Akbarnia et al. | |
| 2014/0277162 A1 | 9/2014 | Kostuik et al. | |
| 2014/0336708 A1 | 11/2014 | Mazda et al. | |
| 2015/0112389 A1 | 4/2015 | Le Couedic et al. | |
| 2015/0119938 A1 | 4/2015 | Lee et al. | |
| 2015/0223845 A1 | 8/2015 | Larroque-Lahitette | |
| 2015/0305782 A1 | 10/2015 | Baccelli et al. | |
| 2015/0320448 A1 | 11/2015 | Legallois | |
| 2015/0342657 A1* | 12/2015 | Voisard | A61B 17/823 606/103 |
| 2015/0366598 A1 | 12/2015 | Douget et al. | |
| 2016/0038194 A1 | 2/2016 | Belliard et al. | |
| 2016/0106478 A1* | 4/2016 | Simpson | A61B 17/842 606/279 |
| 2016/0157896 A1* | 6/2016 | Palmer | A61B 17/7053 606/278 |
| 2016/0213404 A1 | 7/2016 | Al Shail et al. | |
| 2016/0242825 A1 | 8/2016 | Simpson et al. | |
| 2016/0249957 A1 | 9/2016 | Deneuvillers | |
| 2016/0331431 A1 | 11/2016 | Gephart | |
| 2017/0172633 A1 | 6/2017 | Simpson et al. | |
| 2018/0014857 A1* | 1/2018 | Albert | A61B 17/8685 |
| 2018/0021077 A1 | 1/2018 | Simpson et al. | |
| 2018/0110544 A1* | 4/2018 | Simpson | A61B 17/7022 |
| 2018/0153591 A1* | 6/2018 | Schafer | A61B 17/8869 |
| 2018/0263668 A1 | 9/2018 | Hsu et al. | |
| 2018/0289404 A1* | 10/2018 | Shoshtaev | A61B 17/7053 |
| 2018/0296251 A1* | 10/2018 | Palmer | A61B 17/7086 |
| 2018/0353217 A1* | 12/2018 | Rice | A61B 17/8869 |
| 2019/0059958 A1* | 2/2019 | Mast | A61B 17/7022 |
| 2020/0078067 A1 | 3/2020 | Gephart et al. | |

FOREIGN PATENT DOCUMENTS

| | | |
|---|---|---|
| AU | 2014201339 A1 | 10/2014 |
| EP | 2725993 B1 | 6/2012 |
| EP | 2730242 A1 | 9/2013 |
| EP | 2716262 B1 | 9/2014 |
| WO | 2002009604 | 2/2002 |
| WO | 2006119447 | 11/2006 |
| WO | 2013001180 | 1/2013 |
| WO | 2016116692 | 7/2016 |

OTHER PUBLICATIONS

Feb. 4, 2021, PCT/US2020/054610, Written Opinion (4 pgs).
NPL: Biomechanical Evaluation of Spinal Fixation Devices: II. Stability Provided by Eight Internal Fixation Devices, Published May 15, 1988, (6 pgs).
Machine Translation: WO2016116692, dated Jul. 28, 2016, Pasquet et al. (11 pgs).
Machine Translation: EP2716262B1, dated Sep. 4, 2014 Medicrea International, (17 pgs).
Machine Translation: WO2013001180, dated Jan. 3, 2013, Implanet, Societe Anonyme (11 pgs).
Machine Translation: EP2725993B1, dated Jun. 27, 2012, Implanet, Societe Anonyme (21 pgs).

* cited by examiner

TETHER TENSIONING INSTRUMENTATION AND RELATED METHODS

SUMMARY

Disclosed herein are various embodiments of tether tensioning instruments that may be used to increase tension on a tether preferable used in connection with a tether clamping assembly, along with various other inventive methods for using such instruments. In preferred embodiments, the tether tensioning instrument may be used in connection with a self-locking tether clamping implant/assembly. The inventive devices, features, and methods disclosed herein may be particularly suitable for use in connection with spinal fixation. However, it is contemplated that the inventive features, and methods disclosed herein may also be used in other medical procedures, such as bone fracture repair, cardiac procedures, and the like.

In a more particular example of a tether tensioning instrument, such as a spinal fixation tether tensioning instrument, the instrument may comprise a handle and a tensioner base coupled with the handle, wherein at least a portion of the tensioner base is slidably or otherwise movably coupled to the handle. The instrument may further comprise a tether coupling member coupled with the tensioner base and configured to fixedly engage a tether of a spinal fixation system and a tensioner tip movably coupled with the tensioner base. At least a portion of the tensioner base may be biased away from the tensioner tip. The instrument may be configured to allow for stepwise movement of the tensioner tip away from the tensioner base to increase tension between the tether and an element of the spinal fixation system.

In some embodiments, the spinal fixation tether tensioning instrument may comprise one or more components configured to be removed and recoupled together in between surgical procedures. In some such embodiments, the tensioner base may be removable from the handle.

In some embodiments, the tensioner tip may be removable from the handle. The instrument may therefore, in some such embodiments, be modular such that one or both of the tensioner tip and the tensioner base is configured to be removed and replaced with an alternative corresponding component having distinct characteristics relative to the at least one of the tensioner tip and the tensioner base, such as different spring strengths, tip engagement features, sizes, etc.

In some embodiments, the tensioner tip may be spring-loaded to bias an element of the spinal fixation system, such as an outer clamping piece of a clamping assembly, distally during use.

Some embodiments may further comprise a shaft extending from or otherwise coupled to the tensioner tip, which shaft may be configured to extend into the tensioner base to allow the tensioner tip to be slidably coupled with the tensioner base. In some such embodiments, the shaft may comprise a plurality of teeth configured to engage a pawl to allow the tensioner tip to slidably move with respect to the tensioner base in a stepwise manner.

In another example of a tether tensioning instrument for a medical procedure according to other embodiments, the instrument may comprise a handle and a tensioner base coupled with the handle. The instrument may further comprise a tether coupling member configured to fixedly engage a tether of a spinal fixation system and a spring-loaded tensioner tip movably coupled with the tensioner base. The instrument may be configured to allow for movement of the tensioner tip away from the tensioner base to increase tension between the tether and an element of the spinal fixation system. The spring-loaded tensioner tip may be configured to engage an element of the spinal fixation system so as to bias the element of the spinal fixation system received by the spring-loaded tensioner tip in a distal direction but allow for movement of the element of the spinal fixation system received by the spring-loaded tensioner tip in a proximal direction relative to the tether tensioning instrument.

In some embodiments, at least a portion of the tensioner base is slidably or otherwise movably coupled to the handle.

Some embodiments may further comprise a tether coupling member coupled with the tensioner base, which tether coupling member may be configured to allow the tether to be wrapped around the tether coupling member and/or locked in place thereon.

In some embodiments, the tensioner base may be slidably coupled with the handle. In some embodiments, at least a portion of the tensioner base may be biased away from the tensioner tip, such as by providing a spring in the tensioner base and/or a slider positioned within a chamber of the tensioner base.

Some embodiments may further comprise a tension gauge operably coupled with the tensioner base. The tension gauge may be configured to provide an indication of the position of the tensioner base relative to the handle and/or the current tension on the tether. For example, the tension gauge may be configured to provide an indication of the position of the tensioner base relative to the handle, which position may correspond with the tension on at least a portion of the tether during use.

In some embodiments, the instrument may be configured to allow for stepwise movement of the tensioner tip away from the tensioner base to increase tension between the tether and a clamping assembly of the spinal fixation system.

In an example of a method for fixation and/or tensioning of a tether to an anatomical feature of a patient, the method may comprise extending a flexible tether in a loop around an anatomical feature of a patient, such as a spinal lamina or other spinal feature. The flexible tether may then be extended through a tether clamping assembly, such as extending the tether through one or more passages defined by inner and outer clamping pieces of such a tether clamping assembly. A portion of the tether clamping assembly may then be coupled with a tensioner tip of a tether tensioning instrument, wherein the tensioner tip is slidably or otherwise movably coupled with a tensioner base of the tether tensioning instrument. One or both of the free ends of the tether may then be fixedly engaged or otherwise coupled with a portion of the tether tensioning instrument, such as a tensioner base of the tether tensioning instrument. The tether tensioning instrument may then be used to increase tension on the tether, which may result in temporary unlocking of the tether clamping assembly and/or decreasing a size of the loop as the tension is increased, preferably automatically as the tension is increased using the instrument.

In some implementations, the tether clamping assembly may comprise an inner coupling piece nestably coupleable within an outer coupling piece, wherein the tether is configured to extend through opposing passages defined by opposing surfaces of the inner and outer coupling pieces, and wherein the step of positioning the flexible tether through a tether clamping assembly comprises extending the tether through the opposing passages.

In some implementations, actuating the tether tensioning instrument to increase tension on the tether may take place by pulling a lever on the handle. In some such implementations, pulling the lever may result in advancement of a ratcheting mechanism of the tether tensioning instrument.

Some implementations may further comprise releasing the tension on the tether, which may be performed, at least in part, by actuating a trigger of the handle.

In some implementations, the tether clamping assembly may be configured to automatically self-lock the tether to the anatomical feature to maintain the size of the loop following release of the tension on the tether. This may allow for application of a final locking cap to the tether following release of the tension from the instrument, if desired.

The features, structures, steps, or characteristics disclosed herein in connection with one embodiment may be combined in any suitable manner in one or more alternative embodiments.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

A detailed description of apparatus, systems, and methods consistent with various embodiments of the present disclosure is provided below. While several embodiments are described, it should be understood that the disclosure is not limited to any of the specific embodiments disclosed, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

Apparatus, methods, and systems are disclosed herein relating to spinal fixation or other bone fixation. In some embodiments, tether tensioning instruments may be provided that may be used to increase tension on a tether, which may preferably be used in connection with tether clamping assemblies used to clamp a tether about a spinal feature to assist in spinal fixation. In preferred embodiments, the instrument may be used in connection with clamping assemblies configured such that one or more portions of a tether may be self-locked therein without requiring any additional locking elements, features, or steps. In this manner, for example, a tether may be looped around a spinal feature or other anatomical feature, coupled with a fixation element, such as a rod, and then locked in place to stabilize the anatomical feature. In some embodiments, the instrument may be used to both unlock the self-locking feature of the clamping assembly and increase tension on the free ends of the tether, which may result in decreasing a size of the loop about a spinal or other anatomical feature.

The embodiments of the disclosure may be best understood by reference to the drawings, wherein like parts may be designated by like numerals. It will be readily understood that the components of the disclosed embodiments, as generally described and illustrated in the figures herein, could be arranged and designed in a wide variety of different configurations. Thus, the following detailed description of the embodiments of the apparatus and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified. Additional details regarding certain preferred embodiments and implementations will now be described in greater detail with reference to the accompanying drawings.

Figure 1:
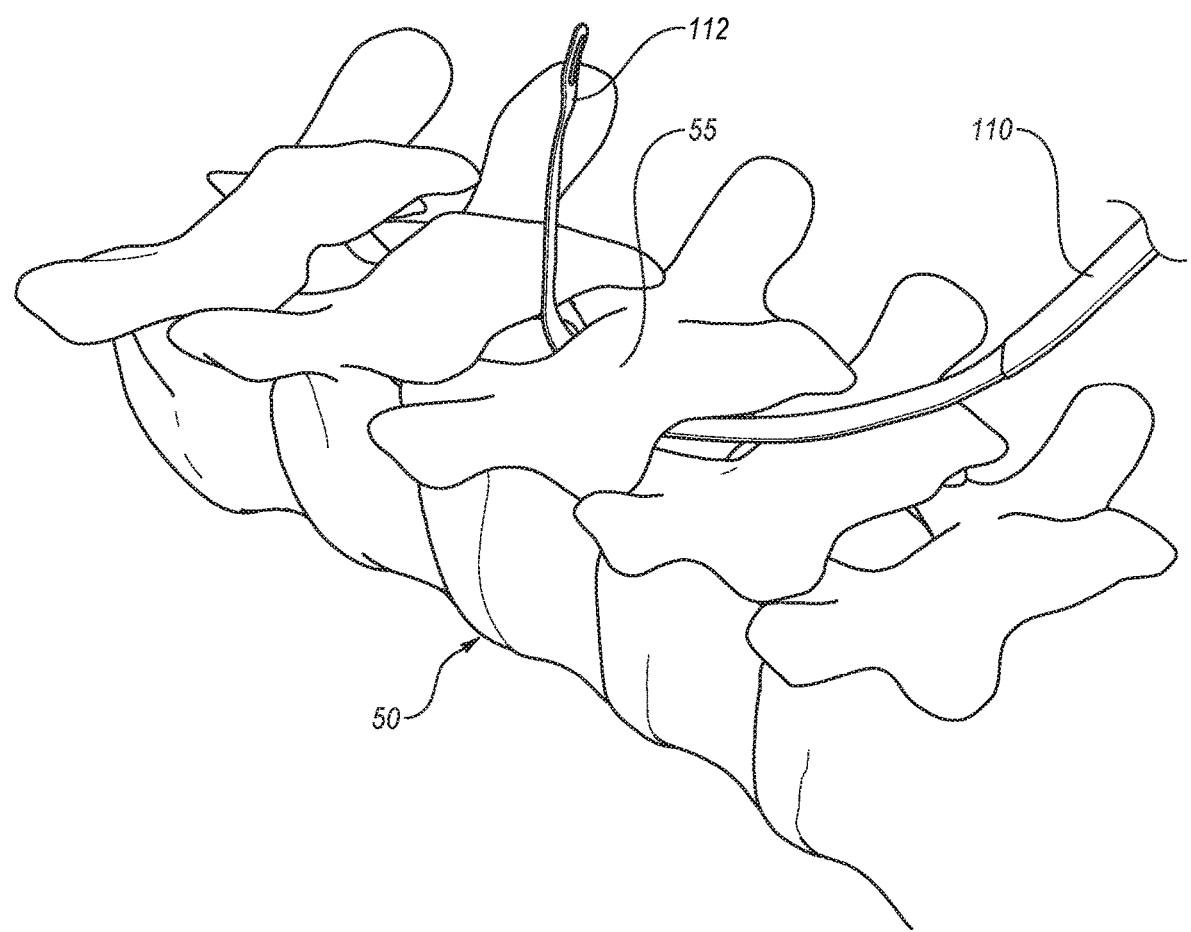
FIG. 1 depicts a tether being extended about a spinal feature.

FIG. 1 depicts a spinal column having a plurality of vertebral bodies 50 during an early stage of a surgical procedure involving fusionless spinal fixation. It should be appreciated that the instruments, features, and/or method steps described herein may, however, be used in connection with other surgical procedures in which it may be desired to apply tension to a tether or other component, such as spinal fusion procedures, bone fractures, cardiac procedures, and the like. In the depicted method, however, a tether 110 is provided with a leader 112, which may comprise a stiffer material compared to the primary portion of tether 110 to facilitate passing the tether 110 beneath a lamina 55 or another structure of the spinal column.

Figure 2:
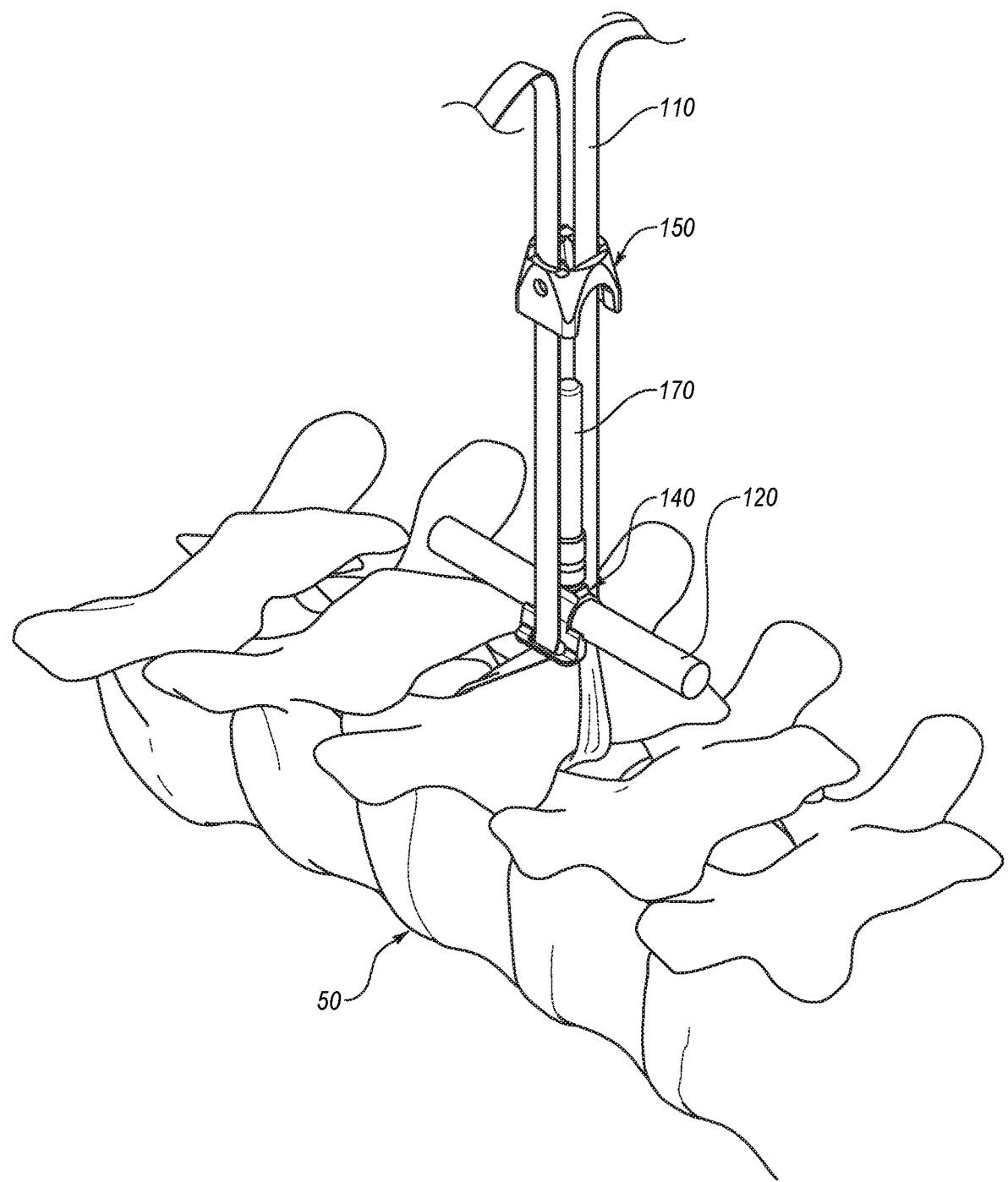
FIG. 2 depicts the tether being extended through a tether clamping assembly according to some embodiments.
Figure 3:
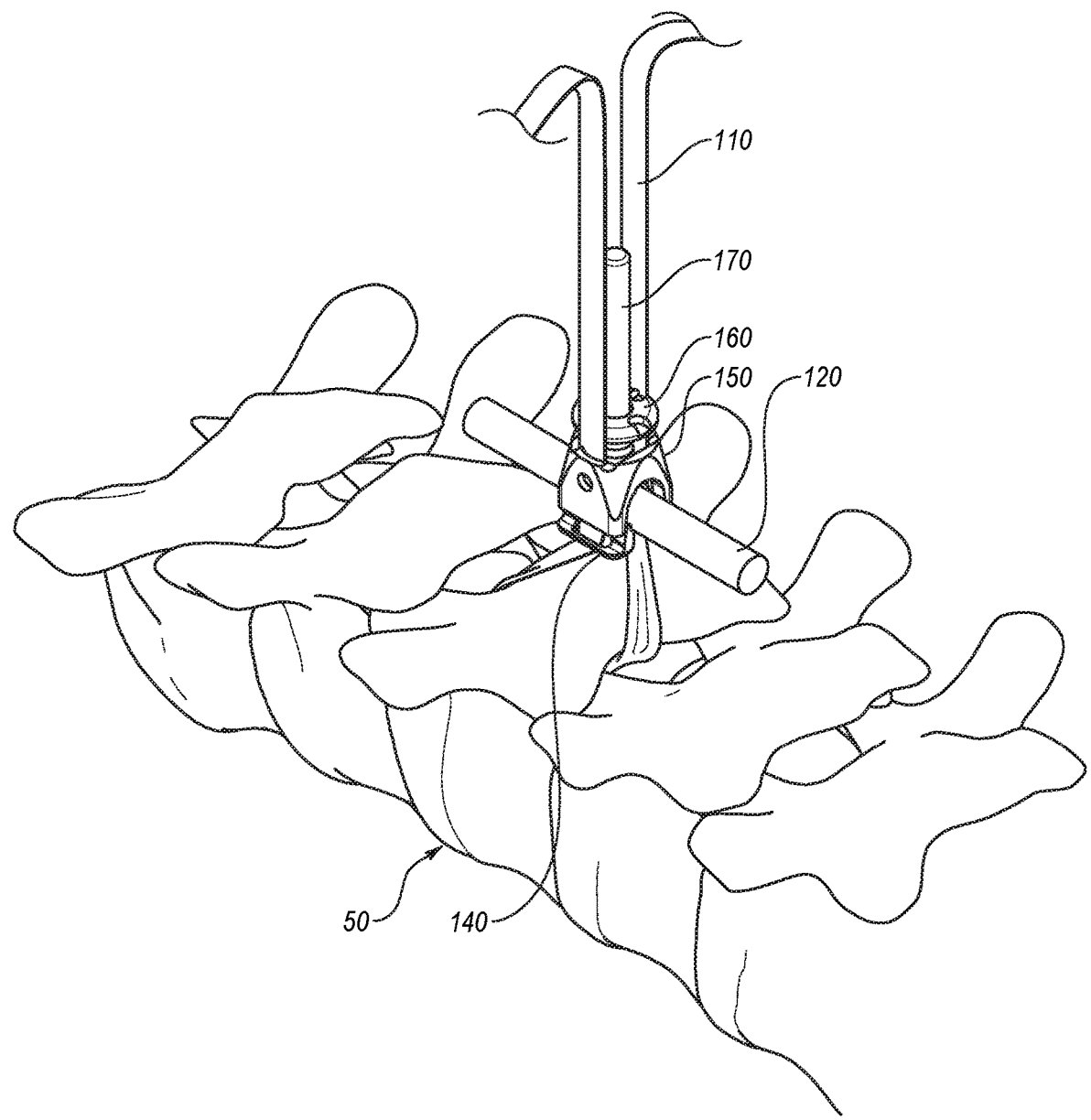
FIG. 3 depicts an outer clamping member of the tether clamping assembly of FIG. 2 being coupled with an inner clamping member to define opposing passages therethrough for the tether.

FIGS. 2 and 3 illustrate additional steps in the aforementioned procedure. In these steps, a clamping assembly is used that comprises a first coupling piece 140, which may comprise an inner coupling piece, and a second coupling piece 150, which may comprise an outer coupling piece, which is configured to be nestably coupled with the first/inner coupling piece 140. The clamping assembly defines two opposing passages configured to receive and engage portions of tether 110 therein, as shown in FIGS. 2 and 3. The first passage may be defined at least in part (in some such embodiments, wholly) by a first external surface of the first/inner coupling piece 140 and first internal surface of the second/outer coupling piece 150.

The second passage may be configured to receive a second portion of the tether 110 therethrough so as to define a loop for engaging a spinal feature of a patient, such as the lamina 55 depicted in FIGS. 1-3. The second passage may also be defined at least in part (in some such embodiments, wholly) by a second external surface of the first/inner coupling piece 140 and a second internal surface of the second/outer coupling piece 150. The first and second passages are configured such that the tether 110 can be clamped in between the first coupling piece 140 and the second coupling piece 150 so as to provide a force differential between extending the tether 110 through the first and second passages in a first direction and in a second direction at least substantially opposite the first direction to facilitate tightening the loop around the spinal feature while inhibiting loosening of the tether 110 around the spinal feature.

In some embodiments and/or implementations, the clamping assembly is self-locking. In preferred embodiments, the clamping assembly may be configured such that one or more portions of tether 110 may be self-locked therein without requiring any additional locking elements, features, or steps. In this manner, for example, a tether 110 may be looped around a spinal feature or other anatomical feature, coupled with a fixation element, such as a rod 120, and then locked in place to stabilize the anatomical feature. Thus, again, in preferred embodiments and implementations, by advancing tether 110 through one or both passages of the tether clamping assembly, the tension on tether 110 alone results in a tightening, and preferably a locking, of tether 110 in the clamping assembly. In order words, upon extending respective tether portions through the aforementioned passages and applying tension in the upward direction (relative to the orientation depicted in FIGS. 2 and 3), the tether portions retain the applied tension and are prevented, or at least inhibited, from being pulled in the opposite, downward direction. Although a locking cap may be used with the assembly to finalize the locking of the tether in place about a spinal or other anatomical structure, such as the locking cap 160 shown in FIG. 3 it should be understood that, preferably, this tension alone results in an at least temporary locking of the tether to the structure. As also shown in FIGS. 2 and 3, a shaft portion 170 of inner coupling piece 140—which, as discussed below, may be frangible and/or otherwise removable—may extend through an opening in outer coupling piece 150 and may extend into an instrument used to tension tether 110 during use.

Additional details of various tether clamping assemblies that may be used in connection with one or more of the instruments and/or methods disclosed herein can be found in U.S. Patent Application Publication No. 2019/0175223 titled "Nesting Tether Clamping Assemblies and Related Methods and Apparatus," which is hereby incorporated by reference in its entirety.

Figure 4:
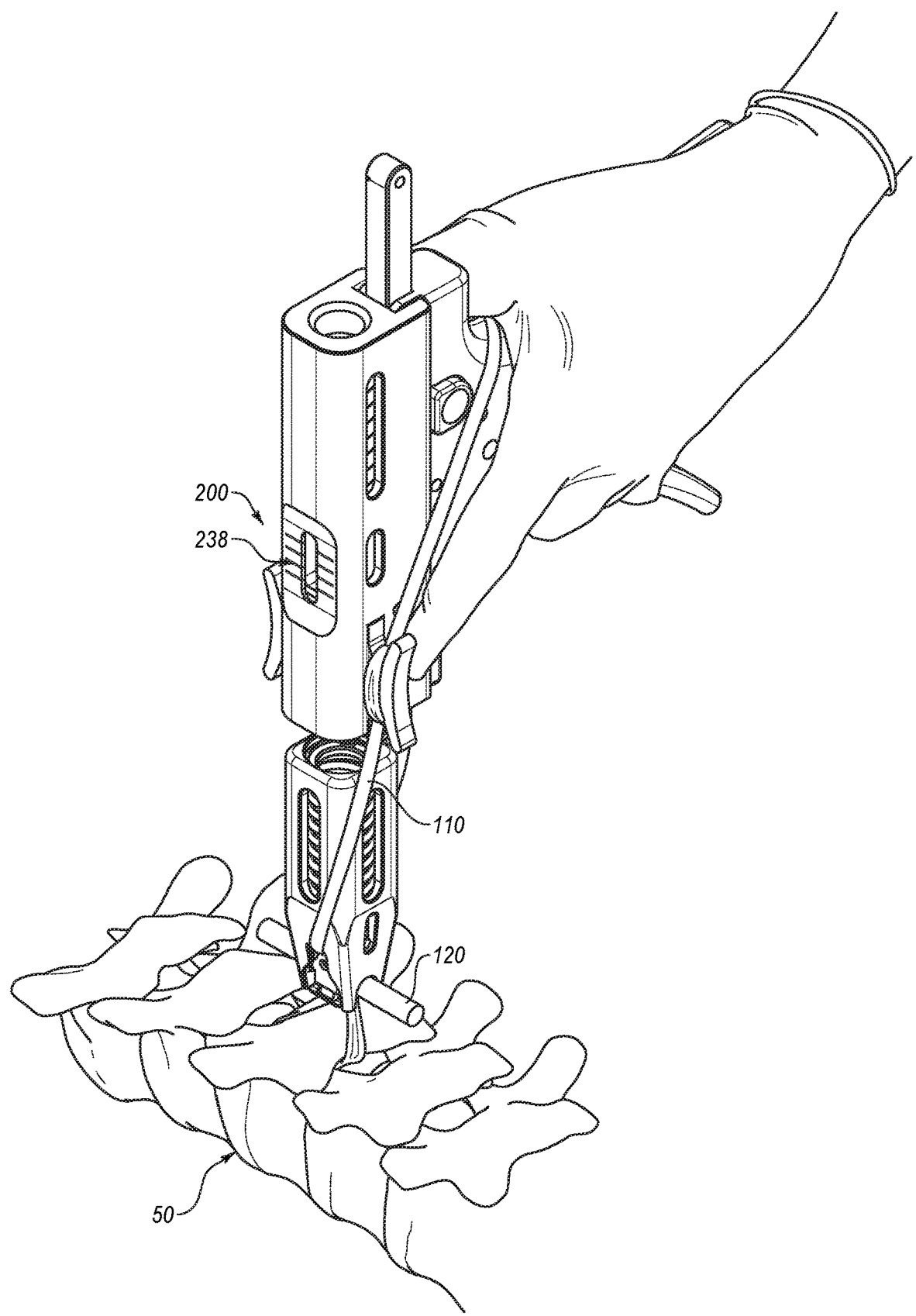
FIG. 4 depicts a tether tensioning instrument engaging the tether clamping assembly and tether to increase tension on the tether to both temporarily unlock the tether clamp provided by the tether clamping assembly and decrease the size of the loop about the spinal feature.

FIG. 4 illustrates a tensioning instrument 200 according to some embodiments being used to tension and lock tether 110 about lamina 55 within the aforementioned clamping assembly comprising inner coupling/clamping member 140 and outer coupling/clamping member 150. Tensioning instrument 200, which is shown and described in greater detail below with reference to other figures, is shown in FIG. 2 being used to simultaneously unlock the self-locking clamp provided by the clamping assembly and apply tension to decrease the size of the loop defined by tether 110 around the adjacent anatomical feature (lamina 55). Upon releasing this tension, the clamping assembly automatically locks in place, which lock may in some embodiments and implementations be maintained by an optional locking cap.

Figure 5A:
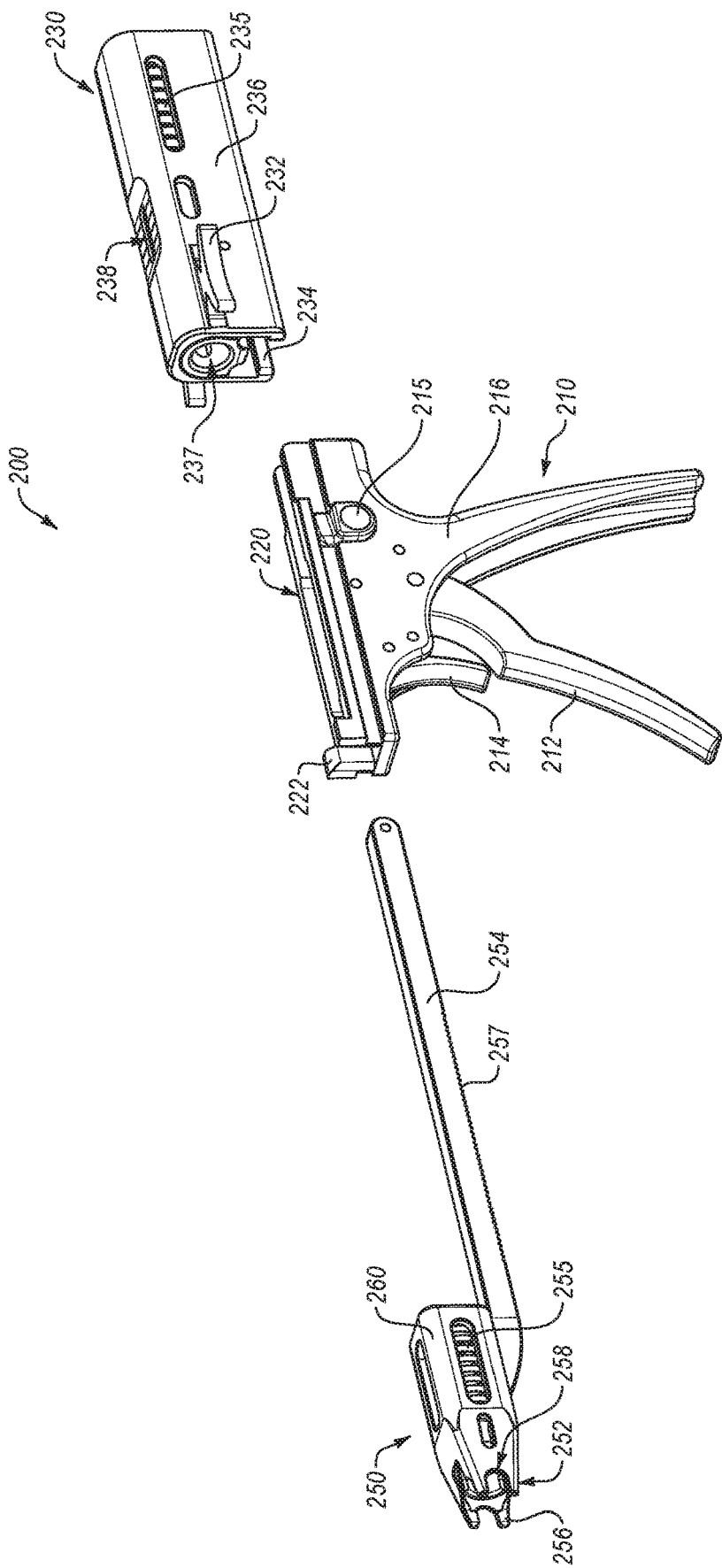
FIGS. 5A and 5B are exploded perspective views of a tether tensioning instrument according to some embodiments.
Figure 5B:
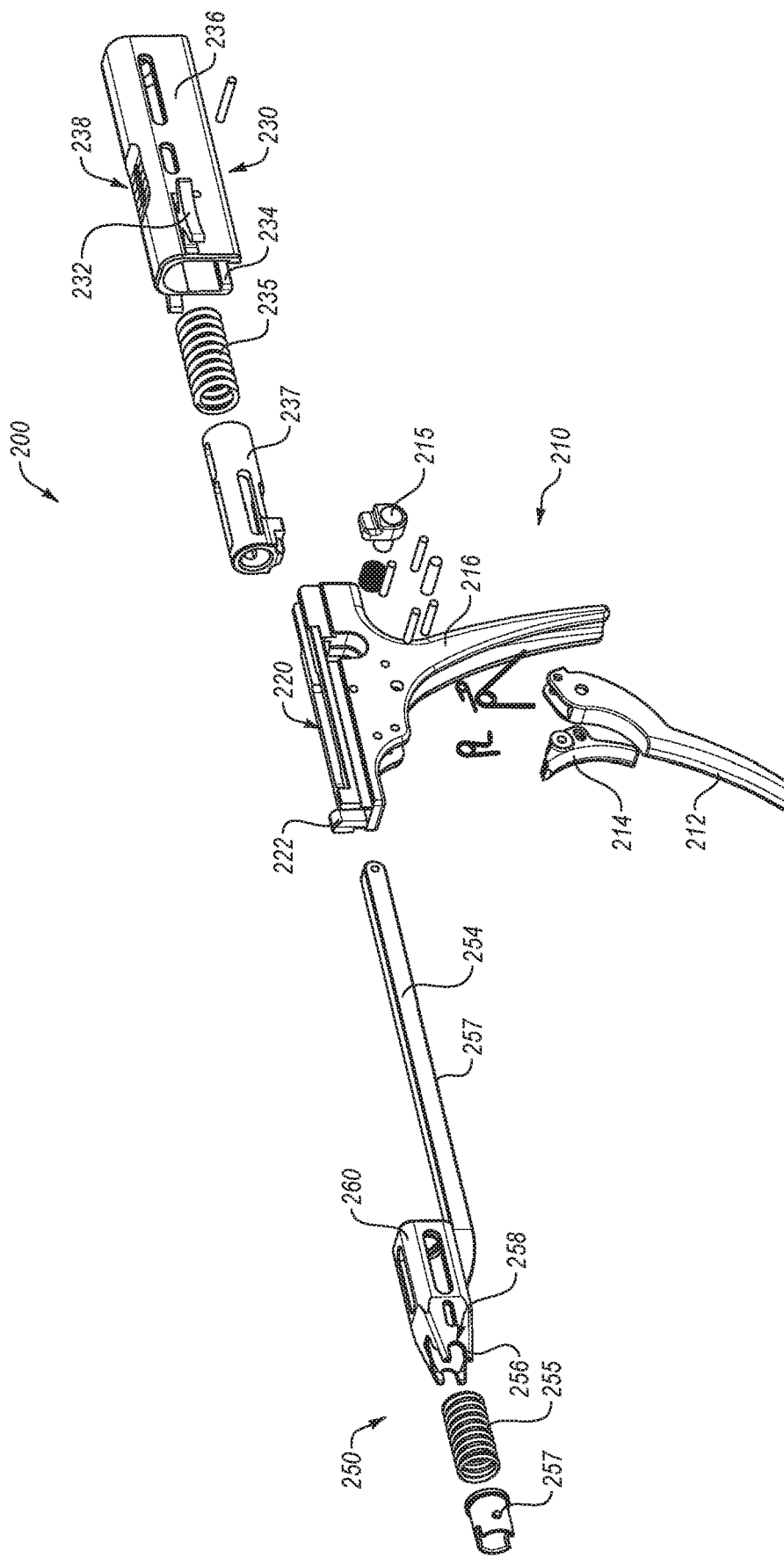

FIGS. 5A and 5B are exploded views of the instrument 200 illustrating various important functional aspects, elements, and features of certain preferred embodiments. As shown in FIG. 5A, for example, tensioning instrument 200 comprises a handle 210 that is coupled with a tensioner base 230 and a tensioner tip 250. In preferred embodiments, tensioning instrument 200 is modular in that one or more elements of the instrument may be removed therefrom and, in some cases, replaced with another element either identical to or functionally similar to the original element.

For example, in some embodiments, the tensioner base 230 and/or tensioner tip 250 may be removed to allow for cleaning and/or sterilization between uses. In some embodiments and implementations, tensioner base 230 and/or tensioner tip 250 may be removed and replaced with alternative components having different uses, features, and/or specifications. For example, in some embodiments, a tensioner base having a spring or other biasing means of a different strength than tensioner base 230 may be used, if desired. Similarly, an alternative tensioner tip, such as, for example, a tensioner tip having a different spring/biasing strength, a different number of ratcheting teeth, and/or a different type of coupling features for coupling with a fixation assembly may be used as a replacement for tensioner tip 250.

Handle 210 may therefore comprise one or more elements configured to facilitate removal and/or recoupling of one or more other elements of instrument 200. For example, handle 210 comprises a pair of rails 220 configured to slidably engage a similar pair of rails 234 on tensioner base 230. A pair of stops 222 may be provided, which may engage one or more corresponding surfaces of tensioner base 230 (more particularly, tensioned slider 237 of tensioner base 230) in order to stop and lock base 230 to handle 210. Release actuator 215 may also be provided to unlock tensioner base 230 from handle 210. In some embodiments, actuator 215 may be spring-loaded and may comprise a button that, while being pushed, recesses a locking surface that normally prevents tensioner base 230 from being slid in an unlocking direction with respect to handle 210. In some preferred embodiments, this locking surface may be ramped so as to allow base 230 to be slidably received on handle 210 in one direction by recessing spring-loaded actuator 215, after which actuator 215 may pop back out to provide the aforementioned locking surface.

Other features of handle 210 that can be seen in FIGS. 5A and 5B include a tensioning lever 212, which, as discussed below, can be used to increase the tension on a tether, in some embodiments in a ratcheting or otherwise stepwise manner. A trigger 214 may also be provided, which, due to the presence of ratcheting teeth or, in other embodiments, other locking features, may be used to release a lock that may otherwise prevent tip 250 from being retracted towards base 230 and/or handle 210.

By contrast, by squeezing lever 212 against grip 216 of handle 210, tip 250 is advanced away from handle 210 and/or base 230 (otherwise stated, handle 210 and/or base 230 are pushed away from tip 250). As discussed below in connection with FIGS. 6A and 6B, this may be accomplished by providing a pawl 213 that is pivotably coupled with handle 212 and advances a set of teeth thereon that engage a series of similar teeth formed on tip 250 and then lock in place to prevent movement of tip 250 in the opposite direction.

Additional functional elements of tensioner base 230 include a housing 236 within which is positioned slider 237 and spring 235. Slider 237 is slidably positioned within the depicted chamber of housing 236 adjacent to spring 235 so that slider 237 is biased in one direction (the proximal direction in the depicted embodiment) relative to the adjacent chamber/housing 236, which itself is slidable relative to handle 210. By providing one or more tether coupling members 232, which are configured to fixedly engage a tether 110, this configuration allows for more precise tensioning of the tether 110 and may further allow for inclusion of a tensioning gauge 238.

Tensioning gauge 238 may comprise a window, which, in the depicted embodiment, is formed on a top portion of housing 236, and allows viewing of the position of slider 237 therewithin. Thus, by providing one or more markings (a simple tick mark will suffice for some embodiments and purposes) on a portion of slider 237 that is visible through the aforementioned window, the extent to which slider 237 has been moved vis-à-vis handle 210, which may correspond with the tension being applied to tether 110, may be determined by viewing the position of the slider 237 within the window. In some embodiments, alphanumeric or other markings, such as tick marks, as shown in FIG. 4, may be provided adjacent the window, which may be used to more precisely gauge the current tension. FIG. 6B depicts instrument 200 under such tension and illustrates how, under such tension, the spring-loaded slider 237 stays fixed vis-à-vis handle 210 while the outer housing 236 slides forward to increase the bias provided by spring 235 during use and, as mentioned above, in some embodiments, provide an at least general indication (specific upon proper calibration) of the current tension being applied.

In the depicted embodiment, tether coupling members 232 are provided on both sides of tensioner base 230. Tether coupling members 232 comprise opposing grooves although, as those of ordinary skill in the art will appreciate, in other embodiments, a single tether coupling member 232 may be provided and/or may comprise only a single such groove. Preferably, the grooves defined by one or both of the tether coupling members 232 have, at least in part, a portion that is smaller in width/size than that of the tether 110 being used, which may allow the tether 110 to be pinched therein to provide additional locking forces. As shown in FIG. 4, the tether may also, or alternatively, be wrapped around and/or tied on the tether coupling member(s) 232. In addition, a wide variety of other tether coupling members are contemplated, such as hooks, bars, clasps or other closable pinching mechanisms, and the like.

Tensioner tip 250 comprises a shaft 254 having a plurality of ratcheting teeth 257 formed thereon. Shaft 254 is configured to be slidably received in an opening defined within handle 210. As best shown in the cross-sectional views of FIGS. 6A and 6B. This opening is defined in part by slider 237 of tensioner base 230 when tensioner base 230 is coupled with handle 210.

Tip 250 further comprises a spring 255 positioned within a chamber 260 that is rigidly coupled to shaft 254. A distal implant engaging end 252 of tip 250 comprises a plurality of prongs 256 that may collectively define a pair of opposing grooves 258 for receiving a rod 120 or another elongated fixation member. As shown in FIG. 5B, some embodiments may further comprise an implant engaging member 257, which may be slidably positioned within the chamber 260 and may be biased towards the distal end of the instrument 200 using spring 255 or another suitable biasing member. By providing a spring-loaded tip in this manner, the outer clamping piece 150 may be allowed to "float" or move slightly in the proximal direction to unlock the tether 110 while it is being tensioned/tightened. Moreover, biasing the outer clamping piece 150 towards the inner clamping piece 140 facilitates re-engagement of the self-locking mechanism of the clamping assembly mentioned throughout this disclosure following release of the tension on the opposing ends of the tether 110 by instrument 200.

It may be desirable to provide a floating implant engaging member 257 that is specifically configured to firmly engage a portion of the implant—i.e., in the case of the depicted system, the outer clamping piece 150. However, it is contemplated that, in alternative embodiments, the outer clamping piece 150 or another portion of the implant may directly engage the spring 255 or another biasing member to provide similar benefits.

Figure 6A:
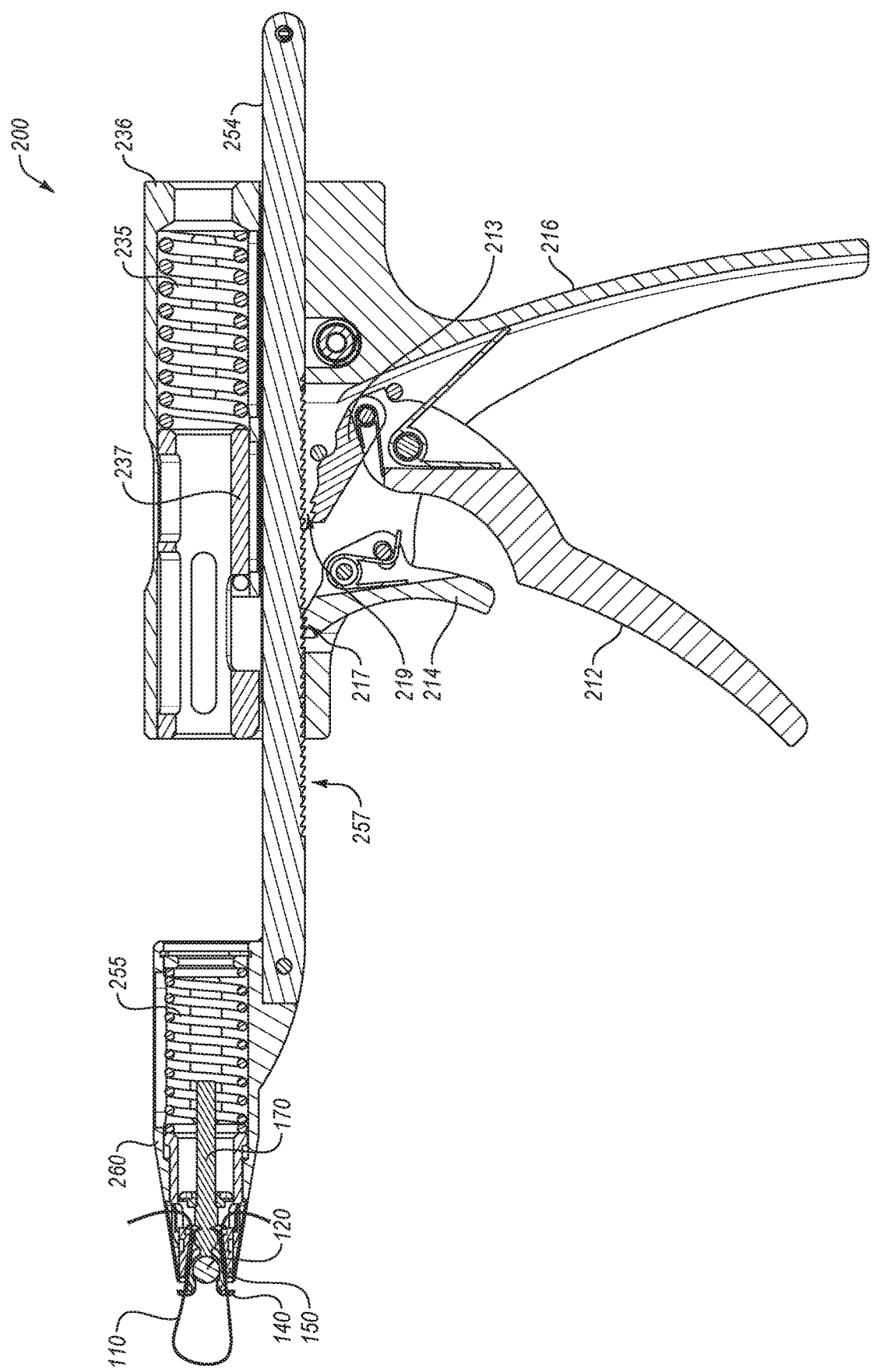
FIG. 6A is a cross-sectional view of the tether tensioning instrument of FIGS. 5A and 5B during a tether tensioning procedure.
Figure 6B:
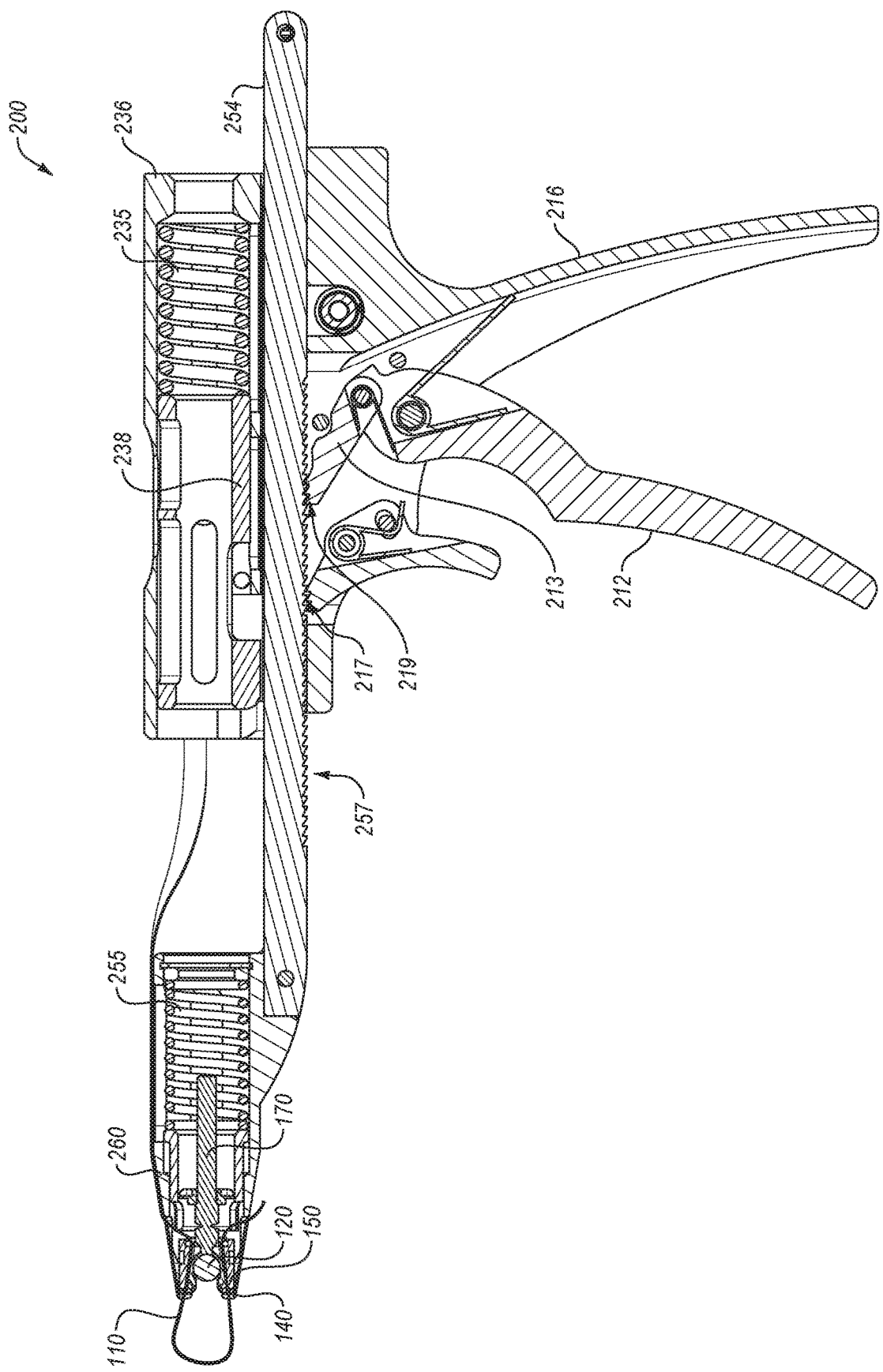
FIG. 6B is a cross-sectional view of the tether tensioning instrument of FIGS. 5A and 5B shown extending the tip from the body of the instrument to increase tension on the free ends of the tether during the tether tensioning procedure.

FIGS. 6A and 6B are cross-sectional views during a tensioning process using instrument 200 and a clamping assembly comprising a tether 110, a rod 120, an inner clamping member 140, and an outer clamping member 150, as previously mentioned. In these figures it can be seen that lever 212 is operably and pivotably coupled with pawl 213, which comprises a set of ratcheting teeth 219 that are configured to engage teeth 257 of shaft 254. After coupling one or both free ends of tether 110 to instrument 200 (preferably to the sliding portion of tensioner base 230, such as to one or both tether coupling members 232), tip 250 may be moved apart from base 230 by squeezing lever 212 against grip 216 of handle 210. This can be done multiple times as desired to increase the tension on tether 110 to a desired level, thereby also decreasing the size of the loop defined by tether 110. By way of the various springs and levers within instrument 200, teeth 219 of pawl 213 engage teeth 257 and forces shaft 254 distally, as shown in FIG. 6B. Releasing lever 212 causes these teeth to disengage, as shown in FIG. 6A. Teeth 217 on trigger 214, however, remain engaged with teeth 257 to prevent tip 250 from moving proximally towards handle 210. Tip 250 may be moved away from handle 210 following a procedure, in some cases removed entirely to allow for cleaning and/or replacement with a different tip, by simply pulling tip 250 away from handle 210 and/or base 230.

As shaft 254 advances distally, the distance between tip 250 and the rest of instrument 200 increases and, due to the engagement of the tether 110 with a proximal portion of the instrument 200, increases tension on the tether 110. As also shown in FIG. 6B, as this tension increases, housing 236, which is slidable/movable relative to handle 210, moves distally relative to handle 210 and compresses spring 235.

In certain embodiments of methods for tensioning a tether during a surgical procedure, such as tensioning a tether about a spinal feature for a fusionless spinal fixation procedure, the tether may initially be looped around the spinal feature or other anatomical feature. One or both sides of the tether may then be positioned within a tether clamping assembly, such as in between inner and outer nestable clamping pieces of a clamping assembly. A rod or other elongated fixation member may also be coupled with the clamping assembly, such as within a slot of the outer clamping piece.

In embodiments having a locking cap, the locking cap may be seated but not fully locked in place. In some embodiments and implementations, a driver may be used to apply the locking cap. In embodiments comprising a clamping assembly having a guide post, such as shaft portion 170 of inner coupling piece 140, the guide post may be inserted into the driver to facilitate this step. Similarly, the shaft portion 170 may be inserted within a hole/tunnel of instrument 200, which may also facilitate a desired coupling and alignment of instrument 200 with the clamping assembly/implant.

Instrument 200 may then be positioned over the clamping assembly/implant preferably with the rod 120 extending through and/or contacting slot 258. The free ends of the tether 110 may then be wrapped around one or both opposing tether coupling members 232 or otherwise coupled to tensioner base 230 or another portion of instrument 200, after which instrument 200 may be actuated, such as by repeatedly squeezing lever 212, to separate tip 250 from base 230 and steadily increase the tension on tether 110. In some embodiments and implementations, the step of actuating the tether tensioning instrument both unlocks the tether clamping assembly and decreases a size of the loop, in some cases simultaneously.

Following sufficient tensioning of tether 110, the release trigger 214 may be actuated to release the tension on tether 110. In embodiments using a self-locking clamping assembly, this step may also result in an at least initial locking/clamping of tether 110 about the anatomical feature, given the tension in the opposite direction (opposite to the free ends of the tether). If desired, the locking cap, such as cap 160, may then be fully tightened to secure the self-locking of the tether 110 about the anatomical feature. Due to the self-locking features of preferred embodiments of the clamping assemblies, the locking cap 160 may be applied while tether 110 is under tension from instrument 200 or, alternatively, after the tension has been released.

Guide post 170 may then be removed. In some embodiments, guide post 170 may therefore have a frangible section to facilitate breaking off guide post 170. In some implementations, the ends of tether 110 may then be cut adjacent to the places at which the opposing ends of tether 110 exit the clamping assembly/implant.

The foregoing specification has been described with reference to various embodiments and implementations. However, one of ordinary skill in the art will appreciate that various modifications and changes can be made without departing from the scope of the present disclosure. For example, various operational steps, as well as components for carrying out operational steps, may be implemented in various ways depending upon the particular application or in consideration of any number of cost functions associated with the operation of the system. Accordingly, any one or more of the steps may be deleted, modified, or combined with other steps.

Further, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced, are not to be construed as a critical, a required, or an essential feature or element.

Those having skill in the art will appreciate that many changes may be made to the details of the above-described embodiments without departing from the underlying principles of the invention. The scope of the present inventions should, therefore, be determined only by the following claims.

The invention claimed is:

1. A method for fixation of a tether to an anatomical feature of a patient, the method comprising the steps of:
    extending a flexible tether in a loop around an anatomical feature of a patient;
    positioning the flexible tether through a tether clamping assembly;
    engaging a portion of the tether clamping assembly with a tensioner tip of a tether tensioning instrument, wherein the tensioner tip is movably coupled with a tensioner base of the tether tensioning instrument, and wherein the tensioner tip is spring-loaded;
    fixedly engaging the tether with a portion of the tether tensioning instrument; and
    actuating the tether tensioning instrument to increase tension on the tether in a stepwise manner, wherein the step of actuating the tether tensioning instrument unlocks the tether clamping assembly and simultaneously decreases a size of the loop.

2. The method of claim 1, wherein the anatomical feature comprises a lamina of a spinal column of the patient.

3. The method of claim 1, wherein the tether clamping assembly comprises an inner coupling piece nestably coupleable within an outer coupling piece, wherein the tether is configured to extend through opposing passages defined by opposing surfaces of the inner and outer coupling pieces, and wherein the step of positioning the flexible tether through a tether clamping assembly comprises extending the tether through the opposing passages.

4. The method of claim 1, wherein the step of actuating the tether tensioning instrument to increase tension on the tether comprises pulling a lever on a handle of the tensioning instrument, and wherein pulling the lever advances a ratcheting mechanism of the tether tensioning instrument.

5. The method of claim 4, further comprising releasing the tension on the tether.

6. The method of claim 5, wherein the step of releasing the tension on the tether is performed, at least in part, by actuating a trigger of the handle.

7. The method of claim 5, wherein the tether clamping assembly is configured to automatically self-lock the tether to the anatomical feature to maintain the size of the loop following release of the tension on the tether.

8. The method of claim 4, further comprising the steps of:
    removing the tensioner tip from the tensioner base; and
    removing the tensioner base from a handle of the tether tensioning instrument.

9. The method of claim 1, wherein the step of actuating the tether tensioning instrument to increase tension on the tether comprises advancing the tensioner tip away from the tensioner base.

10. The method of claim 1, wherein the tensioner tip is configured to bias an element of the tether tensioning instrument distally during use.

11. The method of claim 10, wherein the tensioner tip is configured to unlock the flexible tether during tensioning of the flexible tether.

12. The method of claim 11, wherein the tensioner tip is configured to lock the flexible tether upon release of the tension on the flexible tether.

13. The method of claim 1, wherein the step of actuating the tether tensioning instrument to increase tension on the tether in a stepwise manner comprises repeatedly pulling a lever on a handle of the tensioning instrument.

* * * * *